(12) United States Patent
Harris et al.

(10) Patent No.: US 7,112,692 B2
(45) Date of Patent: Sep. 26, 2006

(54) β-KETOPHOSPHONATES

(75) Inventors: Christopher John Harris, Worcester (GB); Alan Craig Smith, Bedworth (GB); Julie Ann Salter, Dudley (GB)

(73) Assignee: Rhodia Consumer Specialties, Limited, Hertfordshire (GB)

( * ) Notice: Subject to any disclaimer, the term of this patent is extended or adjusted under 35 U.S.C. 154(b) by 379 days.

(21) Appl. No.: 10/485,899

(22) PCT Filed: Aug. 23, 2002

(86) PCT No.: PCT/GB02/03922

§ 371 (c)(1),
(2), (4) Date: Mar. 5, 2004

(87) PCT Pub. No.: WO03/027129

PCT Pub. Date: Apr. 3, 2003

(65) Prior Publication Data

US 2004/0267040 A1 Dec. 30, 2004

(30) Foreign Application Priority Data

Sep. 27, 2001 (GB) ................................ 0123202.4

(51) Int. Cl.
*C07F 9/02* (2006.01)

(52) U.S. Cl. ........................................ 558/198; 568/15
(58) Field of Classification Search .................... None
See application file for complete search history.

(56) References Cited

OTHER PUBLICATIONS

Kim et al.: J. Chem. Soc. Perkin Trans. 1, vol. 9, 1997, pp. 1361-1363, XP009000481.
Kim et al.: Synth. Commun., vol. 29, No. 8, 1999, pp. 1271-1275, XP001119775.
Corbel et al.: Synth. Commun., vol. 30, No. 4, 2000, pp. 609-618, XP001119776.

*Primary Examiner*—Sikarl A. Witherspoon
(74) *Attorney, Agent, or Firm*—Frishauf, Holtz, Goodman & Chick, P.C.

(57) ABSTRACT

A method for making β-ketophosphonates by reacting a trialkyl phosphonocarboxylate (such as triethyl phosphonoacetate) with an acyl halide (such as acetyl chloride) in a reaction involving ester formation, followed by decarboxylation, followed by purification. The reaction is run in a single solvent, which is not removed from the reaction mixture until the purification stage. Suitable solvents for this purpose include halogenated aromatic hydrocarbons (such as mono-chlorobenzene).

9 Claims, No Drawings

β-KETOPHOSPHONATES

This application is a U.S. National Phase Application under 35 USC 371 of International Application PCT/GB02/03922 (published in English) filed Aug. 23, 2002.

This invention relates to beta-ketophosphonates and in particular to an improved method for the production of beta-ketophosphonates. The present invention also relates to beta-ketophosphonates produced by way of the aforesaid method.

Beta-ketophosphonates are known as valuable intermediates in the synthesis of α, β-unsaturated carbonyl compounds by the Horner-Wadsworth-Emmons reaction and also for use in the liquid/liquid extraction of metals.

Typically, beta-ketophosphonates are produced by the reaction of the anion of a dialkyl methyl phosphonate with a carboxylic ester or halide, at low temperatures (e.g. −70° C.). The present invention relates to a method in which beta-ketophosphonates are produced more conveniently by the reaction of a trialkyl phosphonocarboxylate, via its magnesium "enolate", with an acyl halide, at ambient temperatures (e.g. 20° C.). This reaction takes place in three stages, namely intermediate ester formation, decarboxylation and purification. Hitherto, the first stage of the reaction has been carried out using dichloromethane as a solvent for the phosphonocarboxylate. The solvent has to be removed at the end of the first (ester formation) stage, only to be added again and subsequently removed again at the beginning and end respectively of the third (purification) stage. The need to add, remove, add and remove dichloromethane has made this reaction uneconomic to work on an industrial scale.

The applicants have unexpectedly found that replacement of the dichloromethane solvent by a halogenated aromatic hydrocarbon avoids the need to strip out the solvent at the end of the first stage of the reaction, reduces hydrolysis of the decarboxylated product at the second stage and improves the purity and yield of the beta-ketophosphonates obtained at the end of the third stage.

Accordingly, the present invention provides a method for the production of a beta-ketophosphonate by the reaction of a trialkyl phosphonocarboxylate with an acyl halide, said reaction proceeding by way of a first, intermediate ester formation, stage, a second, decarboxylation, stage and a third, purification, stage, in which said reaction is carried out in a single solvent, said solvent not being removed until the third, purification stage of said reaction.

Preferably, the solvent used in accordance with the method of the present invention is a halogenated aromatic hydrocarbon. A particularly preferred solvent is monochlorobenzene.

The use of monochlorobenzene (b.p. 132° C.) instead of dichloromethane (b.p. 40° C.) makes the method inherently safer (the solvent acts as a heat-sink for the reaction) as well as more industrially applicable. The need to add more solvent or to dry the crude product of the second, decarboxylation, stage, is avoided. The solvent is removed (e.g. by vacuum-distillation) at the end of the reaction and aqueous work-up procedure.

The first, intermediate ester formation, stage conveniently proceeds by way of a magnesium "enolate" of the starting trialkyl phosphonocarboxylate. This first stage is typically carried out in the presence of a base, with subsequent hydrolysis to produce intermediate ester.

The trialkyl phosphonocarboxylate may suitably be triethyl phosphonoacetate or trimethyl phosphonoacetate. It may conveniently be formed into the corresponding magnesium "enolate" by the action of magnesium chloride.

The base is preferably a tertiary amine such as triethylamine.

The acyl halide may be acetyl chloride or isobutyryl chloride. Other acyl halides include hydrocinnamoyl (3-phenylpropionyl) chloride, valeryl (pentanoyl) chloride and caproyl (hexanoyl) chloride.

Hydrolysis to form the intermediate ester may be achieved by the use of a dilute mineral acid, for example hydrochloric acid.

The second, decarboxylation, stage may be achieved by the addition of a small amount of water to the solution of the intermediate ester in chlorobenzene, followed by heating of the mixture to 100–110° C. Excess water and alcohol, formed as a by-product of the decarboxylation, is distilled from the reactor at this stage.

The product of the second, decarboxylation, stage is then vacuum-stripped to remove the solvent, typically giving rise to a high-purity (more than 98% pure) and a high-yield (more than 95% yield) product.

The present invention further provides beta-ketophosphonates provided by the method hereinabove described.

A preferred embodiment of the present invention will be described by way of the following Examples.

EXAMPLE 1

Preparation of Diethyl-2-oxopropyl phosphonate

A reaction vessel was charged with magnesium chloride (31.7 g) and chlorobenzene (550 g). Triethylphosphonoacetate (74.7 g) was then added to this over a period of 10 minutes at 20° C. Triethylamine (84.2 g) was subsequently added to this mixture at 20° C. over 20 minutes, then stirred for 30 minutes at 20° C. Acetyl chloride (34.9 g) was then added to the reaction mixture at 20° C. over 45 minutes, and stirred for a further 30 minutes at 20° C. The reaction mixture was quenched with 500 g 1M hydrochloric acid, which was added over 10 minutes and stirred for 1 hour at 20° C. The organic and aqueous phases were allowed to separate, and the organic layer containing the intermediate ester was removed from the reactor.

The organic layer was charged to a reactor configured for distillation, together with 9 g of water. The mixture was heated for 4 hours at 110° C. or until product purity, measured by $^{31}$P-NMR, was greater than 98%.

The organic mixture was subjected to an aqueous washing procedure. The organic layer, containing the product, was separated and the chlorobenzene solvent was removed by vacuum stripping to leave the title compound in high yield and purity.

EXAMPLE 2

Preparation of Diethyl-2-oxo-(3-methyl)butyl phosphonate

A reaction vessel was charged with magnesium chloride (19.0 g) and chlorobenzene (330 g). Triethylphosphonoacetate (44.8 g) was then added to this over a period of 10 minutes at 20° C. Triethylamine (50.5 g) was subsequently added to this mixture at 20° C. over 20 minutes, then stirred for 30 minutes at 20° C. Isobutyryl chloride (24.5 g) was then added to the reaction mixture at 20° C. over 40 minutes, and stirred for a further 30 minutes at 20° C. The reaction mixture was quenched with 300 g 1M hydrochloric acid, which was added over 10 minutes and stirred for 1 hour at 20° C. The organic and aqueous phases were allowed to separate, and the organic layer containing the intermediate ester was removed from the reactor.

The organic layer was charged to a reactor configured for distillation, together with 9 g of water. The mixture was heated for 4 hours at 110° C. or until product purity, measured by $^{31}$P-NMR, was greater than 98%.

The organic mixture was subjected to an aqueous washing procedure. The organic layer, containing the product, was separated and the chlorobenzene solvent was removed by vacuum stripping to leave the title compound in high yield and purity.

EXAMPLE 3

Preparation of Dimethyl 2-oxo-(4-phenyl)butyl phosphonate

A reaction vessel was charged with magnesium chloride (19.0 g) and chlorobenzene (300 g). Trimethylphosphonoacetate (36.4 g) was then added to this over a period of 10 minutes at 20° C. Triethylamine (50.5 g) was subsequently added to this mixture at 20° C. over 20 minutes, then stirred for 30 minutes at 20° C. Hydrocinnamoyl chloride (37.1 g) was then added to the reaction mixture at 20° C. over 40 minutes, and stirred for a further 30 minutes at 20° C. The reaction mixture was quenched with 300 g 1M hydrochloric acid, which was added over 10 minutes and stirred for 1 hour at 20° C. The organic and aqueous phases were allowed to separate, and the organic layer containing the intermediate ester was removed from the reactor.

The organic layer was charged to a reactor configured for distillation, together with 6 g of water. The mixture was heated for 4 hours at 110° C. until decarboxylation of the intermediate ester, determined by $^{31}$P-NMR, was complete, then allowed to cool.

The organic layer, containing the product, was separated and the chlorobenzene solvent was removed by vacuum stripping to leave the title compound in high yield and purity.

The invention claimed is:

1. A method for the production of a beta-ketophosphonate by the reaction of a trialkyl phosphonocarboxylate with an acyl halide, said reaction proceeding by way of a first, intermediate ester formation, stage, a second, decarboxylation, stage and a third, purification, stage, in which said reaction is carried out in a single solvent, said solvent not being removed until the third, purification, stage of said reaction.

2. A method according to claim 1, in which the solvent is a halogenated aromatic hydrocarbon.

3. A method according to claim 2, in which the solvent is monochlorobenzene.

4. A method according to claim 1, in which the first stage is carried out in the presence of a base.

5. A method according to claim 4, in which the base is a tertiary amine.

6. A method according to claim 5, in which the base is triethylamine.

7. A method according to claim 1, in which the trialkyl phosphonocarboxylate is triethyl phosphonoacetate or trimethyl phosphonoacetate.

8. A method according to claim 1, in which the acyl halide is acetyl chloride or isobutyryl chloride.

9. A method according to claim 1, in which the acyl halide is hydrocinnamoyl chloride, valeryl chloride or caproyl chloride.

* * * * *